United States Patent
Hallynck et al.

(10) Patent No.: US 12,109,386 B2
(45) Date of Patent: Oct. 8, 2024

(54) ADAPTOR FOR A NEEDLELESS ACCESS DEVICE AND METHOD FOR CONNECTING SAID DEVICE THEREON

(71) Applicant: Becton Dickinson France, Le Pont de Claix (FR)

(72) Inventors: Sylvain Hallynck, Sechilienne (FR); Robin Woolls, Gloucestershire (GB); Lionel Maritan, Pierre-Chatel (FR); Thomas Devouassoux, Saint Martin d'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 388 days.

(21) Appl. No.: 17/162,690

(22) Filed: Jan. 29, 2021

(65) Prior Publication Data

US 2021/0146112 A1 May 20, 2021

Related U.S. Application Data

(63) Continuation of application No. 14/906,378, filed as application No. PCT/EP2014/065744 on Jul. 22, 2014, now Pat. No. 10,933,228.

(30) Foreign Application Priority Data

Jul. 23, 2013 (EP) .................................. 13306066

(51) Int. Cl.
*A61M 39/10* (2006.01)
*A61M 5/34* (2006.01)
*A61M 5/31* (2006.01)

(52) U.S. Cl.
CPC ............ *A61M 39/10* (2013.01); *A61M 5/347* (2013.01); *A61M 39/1011* (2013.01);
(Continued)

(58) Field of Classification Search
CPC ...... A61M 39/1011; A61M 2039/1027; A61M 39/10; A61M 2039/1077
(Continued)

(56) References Cited

U.S. PATENT DOCUMENTS 4,121,587 A 10/1978 Kronman et al.
4,735,441 A 4/1988 Stephens
(Continued)

FOREIGN PATENT DOCUMENTS

CN 101166928 A 4/2008
CN 202569055 U 12/2012
(Continued)

*Primary Examiner* — Phillip A Gray
(74) *Attorney, Agent, or Firm* — The Webb Law Firm

(57) ABSTRACT

An adaptor for connecting a drug delivery device to a needleless access device having a straight external thread, including engagement means for mounting said adaptor on the drug delivery device, and an internal thread intended to cooperate with said external thread on a determined length, said internal thread showing on a distal part of said length a first major diameter mating that of said straight external thread, wherein said internal thread shows on a proximal part of said length a second major diameter, where the second major diameter is strictly smaller than the first major diameter, said internal thread further including a tapered portion linking said proximal part to said distal part.

23 Claims, 2 Drawing Sheets

(52) U.S. Cl.
CPC ... *A61M 5/3134* (2013.01); *A61M 2039/1033* (2013.01); *A61M 2039/1038* (2013.01); *A61M 2039/1077* (2013.01)

(58) Field of Classification Search
USPC .................................................. 604/283, 533
See application file for complete search history.

(56) References Cited

U.S. PATENT DOCUMENTS

| | | |
|---|---|---|
| 5,234,417 A | 8/1993 | Parks et al. |
| 5,405,240 A | 4/1995 | Uno |
| 5,405,340 A * | 4/1995 | Fageol ............... A61M 39/1011 |
| | | 285/247 |
| 5,651,776 A | 7/1997 | Appling et al. |
| 7,243,957 B2 * | 7/2007 | Reynolds, Jr. ...... E21B 17/0423 |
| | | 285/333 |
| 9,017,291 B2 | 4/2015 | Delabie |
| 9,717,855 B2 | 8/2017 | Bosshardt et al. |
| 2001/0003150 A1 | 6/2001 | Imbert |
| 2011/0282295 A1 * | 11/2011 | Pupke ................... A61M 5/347 |
| | | 604/187 |
| 2014/0012204 A1 | 1/2014 | Bosshardt et al. |

FOREIGN PATENT DOCUMENTS

| | | |
|---|---|---|
| EP | 0716860 A2 | 6/1996 |
| JP | S62885 U | 1/1987 |
| JP | H08317994 A | 12/1996 |
| JP | 2012530586 A | 12/2012 |
| JP | 2014502524 A | 2/2014 |
| RU | 94030466 A | 5/1996 |
| WO | 2012049532 A1 | 4/2012 |
| WO | 2013010951 A1 | 1/2013 |

\* cited by examiner

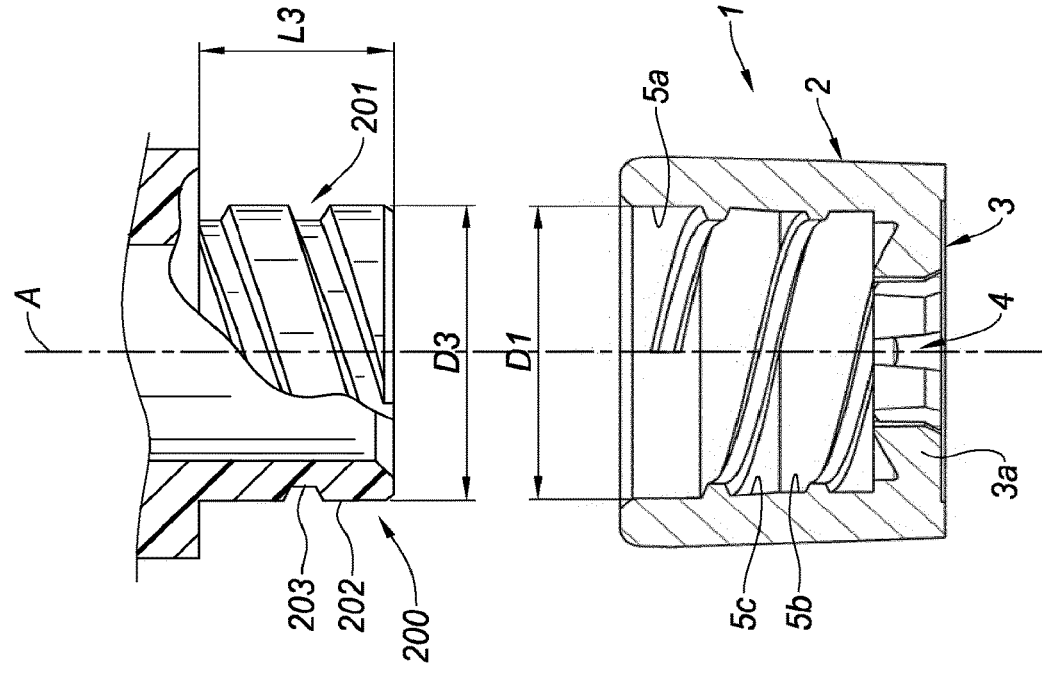
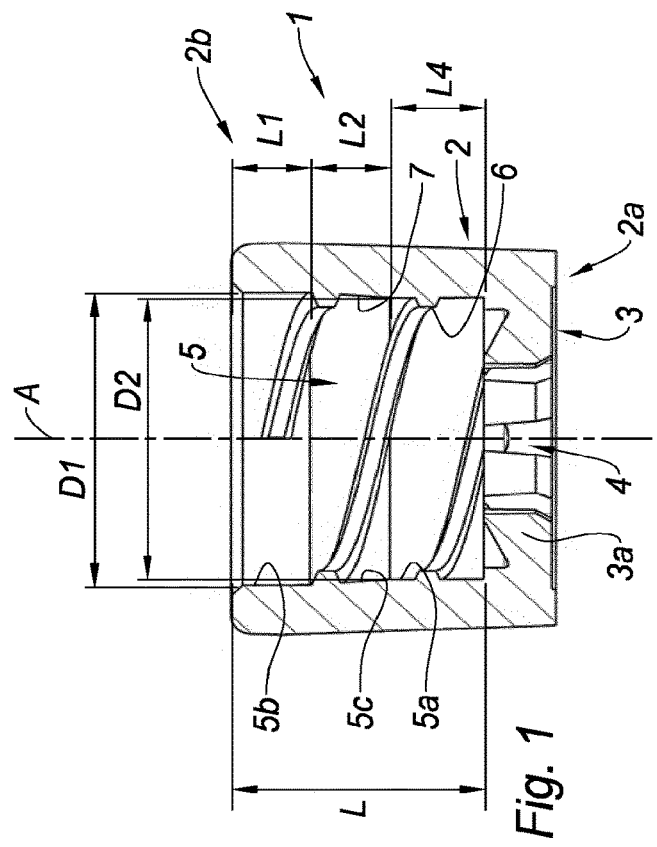

ADAPTOR FOR A NEEDLELESS ACCESS DEVICE AND METHOD FOR CONNECTING SAID DEVICE THEREON

CROSS-REFERENCE TO RELATED APPLICATIONS

This application is a continuation of U.S. patent application Ser. No. 14/906,378 filed Jan. 20, 2016, which is the United States national phase of International Application No. PCT/EP2014/065744 filed Jul. 22, 2014, and claims priority to European Patent Application No. 13306066.5 filed Jul. 23, 2013, the disclosures of which are hereby incorporated in their entirety by reference.

BACKGROUND OF THE INVENTION

Field of the Invention

The present invention relates to an improved adaptor for connecting a drug delivery device to a needleless access device. The invention also relates to a drug delivery device provided with such an improved adaptor. The invention further relates to a method for connecting said adaptor to a needleless access device and to a method for connecting a drug delivery device to a needleless access device via such an adaptor.

Various medical devices are known for transferring and/or storing medical fluids, such as syringes, needle assemblies, perfusion devices, transfusion devices and connectors such as for example IV (intra venous), IM (intra muscular), subcutaneous connectors. It is essential for safety reasons that these various medical devices can be assembled together correctly and securely.

In this view and in order to simplify medical procedures, standardized connecting systems have been developed, which involve the assembly of conical fittings with specific dimensions conforming to criteria defined in ISO 594 standards.

Basically, drug delivery devices, such as for example hypodermic syringes, usually comprise a hollow body forming a reservoir for containing a medical product. In addition, the distal end of the body forming the reservoir usually comprises a distal tip in which an axial passageway is arranged through which the said product is expelled from the reservoir into a needle. For safety reasons, the needle may be provided on a needle hub which is connected to the distal tip only at the time of use.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the drug delivery device the adaptor of the invention is intended to be mounted on, and the "proximal direction" is to be understood as meaning the opposite direction to said direction of injection.

In conformity with the ISO 594 standards, the distal tip of a drug delivery device is conical and shows a 6% tapering, thereby constituting the male part of what is called a Luer connecting system. The female part of the Luer connecting system is for example a corresponding 6% tapering bore of the needle hub intended to be connected to the distal tip. Such a Luer connecting system allows leak-free connections between drug delivery devices and needle hubs for example and provides protection against the contamination of the medical liquid products they contain.

A simple Luer connecting system comprises male and female fittings which simply conform to Luer taper dimensions and which are pressed together and held by friction. Anyway, in order to improve the security and stability of the connection between the male fitting and the female fitting, locking means have been provided, which are called Luer-Lock fittings. In such a case, an outer relief is provided on the female fitting which screws into threads provided in a collar surrounding the male fitting.

When drug delivery devices are made of plastic, the collar surrounding the male fitting, namely the distal tip, may be unitarily molded with the drug delivery device. However, drug delivery devices made of glass usually have a separate collar securely mounted to their distal tip.

Such a separate collar, or also called adaptor, may be used either for glass delivery devices or plastic delivery devices and is usually first mounted to the distal tip of the drug delivery device. The medical instrument intended to be connected to the drug delivery device, such as the needle hub for example, may then be screwed into the adaptor in a second step.

However, in view of improving safety of the healthcare workers and of preventing needlestick injuries, the use of "engineering controls" such as needleless access devices is recommended. Needleless access devices reduce the risk of needle sticks, decrease the risk of accidental exposure to bloodborne pathogens and are also believed to be a key factor in preventing Blood Stream Infections (BSIs).

These needleless access devices are intended to be connected to a drug delivery device via an adaptor as mentioned above. The needleless access devices are particularly useful in case of parenteral administration to a patient for example, where injection is carried out via a perfusion device. In such a case, the needleless access device is the IV (Intra Veinous) line which links the drug delivery device, containing the product to be delivered, to the vein of the patient. Of course, the IV line and the drug delivery device must be assembled together correctly and securely.

Anyway, some needleless access devices have not been originally developed in a view of being connected to a drug delivery device, and they do not conform with the standardized dimensions set forth for luer taper connectors, thereby providing a poor conical fitting in the end potentially leading to a misconnection. In addition, some needleless access devices are provided with internal safety systems which naturally weakens their connection to the drug delivery device. Indeed, such internal safety systems usually comprise a spring biased piece that needs to be displaced in order to allow access to the product. The presence of such springs provide the needleless access devices with high counter forces which need to be fought against at the time the needleless access device is connected to the drug delivery device and during the time the needleless access device is connected to the drug delivery device via the adaptor.

As a result, it may happen that a needleless access device spontaneously unscrews from the adaptor it was previously screwed in, and as a consequence is accidently disconnected from the drug delivery device. In particular, the potential counter force of the needleless access device combined to the fact that the dimensions of the needleless access device may not conform to the standards leads to an unscrewing force which is higher than the resistance of the connection and which may cause untimely disconnection of the needleless access device from the adaptor and therefore from the drug delivery device. This phenomenom may be increased when the drug delivery device and its distal tip are made of glass, as glass surfaces are naturally easy sliding surfaces.

Therefore, there is a need for an improved adaptor enabling to ensure a reliable assembly of a needleless access device to the adaptor, yet without having to apply too high a torque at the time the needleless access device is screwed into the adaptor. Indeed, increasing the torque for screwing a needleless access device into an adaptor mounted on the distal tip of a drug delivery device increases the risk that the adaptor rotates around the distal tip of the drug delivery device. Such a rotation is not desirable as it weakens the fixation of the adaptor on the distal tip and it does not allow the user to determine whether the needleless access device is correctly screwed into the adaptor or not.

There is also a need for a drug delivery device provided with such an improved adaptor.

SUMMARY OF THE INVENTION

An aspect of the present invention is an adaptor intended to be mounted at one of its ends, in particular its proximal end, on a drug delivery device, for example on a distal tip thereof, and at its other end, namely its distal end, to a needleless access device provided with an external thread, allowing a safe connection between the needleless access device and the adaptor, and therefore between the needleless access device and the drug delivery device. In particular, the adaptor of the invention includes a specific internal thread ensuring an optimal fixation of the adaptor onto the needleless access device, so that said needleless access device may not be spontaneously and accidently disconnected from the adaptor in use.

A first aspect of the invention is an adaptor for connecting a drug delivery device to a needleless access device provided with a straight external thread, the adaptor including a globally tubular body having a proximal region and a distal region, said proximal region being provided with engagement means for mounting said adaptor on the drug delivery device, said distal region being provided on its inner wall with an internal thread intended to cooperate with said external thread on a determined length L of said internal thread so as to connect said needleless access device to said adaptor, said internal thread having on a distal part of said length L, said distal part having a length L1, a major diameter D1 of constant value mating that of said straight external thread, wherein said internal thread has on a proximal part of said length L a major diameter D2, where D2 is strictly smaller than D1, wherein said internal thread further includes a tapered portion linking said proximal part to said distal part, said tapered portion having a length L2. In particular, the proximal region of the globally tubular body is adapted to engage the drug delivery device. In particular, the engagement means are provided on the proximal region of the globally tubular body to engage the drug delivery device.

In the present application, "needleless access device" means any device free of needle and intended to be connected to the adaptor, either for allowing the transfer of a product from the drug delivery device to another medical device, such as a pocket drip, a vial, an IV (Intra Venous) line, an IM (Intra Muscular) line, a catheter, or on the contrary for safely closing the filled drug delivery device before its use and for preventing any contamination, like for example a closure cap in the storage position of the drug delivery device.

In the present application "straight external thread" means a ridge wrapped around a cylinder in the form of a helix. In particular, the height of the ridge and the diameter of the cylinder are both constant values. In the present application, "straight internal thread" means a ridge located on the inner wall of a tube in the form of a helix. In particular, the height of the ridge and the inner diameter of the tube are both constant values.

Another aspect of the invention is a drug delivery device including a distal tip defining an axial passageway for the transfer of a product contained in said drug delivery device, further including at least one adaptor as described herein mounted on said distal tip.

Another aspect of the invention is a method for connecting a needleless access device provided with a straight external thread onto an adaptor as described herein including at least the step of screwing said straight external thread into the internal thread of the adaptor on said determined length L of said internal thread.

Another aspect of the invention is a method for connecting a drug delivery device to a needleless access device provided with a straight external thread, including the following steps:
  providing an adaptor as described herein,
  engaging said adaptor on the drug delivery device via the engagement means,
  screwing said straight external thread into the internal thread of the adaptor on said determined length L of said internal thread.

The adaptor of the invention may be used for example for connecting a IV line to a drug delivery device.

The adaptor of the invention allows a safe connection of a needleless access device provided with a straight external thread to the adaptor, and by consequence to a drug delivery device having said adaptor mounted thereon.

Surprisingly, the decrease of the diameter on a proximal part of the length of the internal thread allows better radial interferences between the adaptor and the needleless access device, yet without requiring that a higher torque be exerted for screwing the needleless access device into the adaptor, compared to adaptors of the prior art. The higher friction thereby provided between the needleless access device and the adaptor of the invention allows tightening the screwing and stabilizing the resulting connection. This increased friction is able to compensate the high counter force potentially present in the needleless access device.

In addition, with the adaptor of the invention, only a limited torque, in particular lower than that of adaptors of the prior art provided with conventional straight internal threads, is necessary at the time of screwing the needleless access device into the adaptor, in order to obtain this improved stable connection. The engagement means of the adaptor for mounting the adaptor onto the distal tip of a drug delivery device therefore does not need to be provided with a higher torque resistance.

The risks that a needleless access device screwed into the adaptor of the invention be accidently disconnected are therefore greatly limited. Consequently, the adaptor of the invention allows a reproducible and safe connection of a needleless access device on said adaptor, and by extension to the drug delivery device.

In addition, the decrease of the diameter of the internal thread in the proximal part of its length, said length being measured along the direction of the longitudinal axis A of the tubular body, provides for a thicker wall of the proximal part of the tubular body, thereby increasing the resistance of said tubular body at the time the needleless access device is screwed therein.

The distal part of the internal thread of the adaptor of the invention has a length L1 and a major diameter D1 mating the straight external thread of the needleless device the adaptor is intended to be connected to. The major diameter D1 has therefore a constant value over the length L1 of the distal part of the internal thread and it defines a straight internal thread on the length L1. The distal part of the internal thread of the adaptor of the invention defines therefore a straight internal thread. The distal part of the internal thread is linked to the proximal part, having a major diameter D2 strictly smaller than D1, by a tapered portion of the internal thread. The internal thread of the adaptor of the invention therefore includes a distal part, which is under the form of a straight internal thread, a proximal part having a major diameter less than that of the distal part, and a tapered portion linking the distal part to the proximal part. The value of the major diameter of the tapered portion of the internal thread varies from that of D1 to that of D2.

In embodiments, said proximal part having a length L4, D2 has a constant value over the length L4. The proximal part of the internal thread is therefore a straight internal thread on length L4.

The adaptor of the invention provides for a smooth and progressive screwing of the needleless access device into the adaptor of the invention on the overall length L of the internal thread.

In embodiments, the ratio of D2 to D1 ranges from 0.95 to 0.98. The additional friction force thereby provided between the external thread and the internal thread allows a more secured fixation between the needleless access device and the adaptor of the invention.

In embodiments, the ratio of the length L1 of the distal part to the length L2 of the tapered portion ranges from 0.9 to 1.1, preferably is about 1. Such embodiments provide for an optimized stabilized connection between the needleless access device and the adaptor of the invention.

In embodiments, the ratio of the length L1 of the distal part to the length L4 of the proximal part ranges from 1.125 to 1.325, preferably is about 1.225. In embodiments, the ratio of the length L2 of the tapered portion to the length L4 of the proximal part ranges from 1.125 to 1.325, preferably is about 1.225. Such embodiments provide for an optimized stabilized connection between the needleless access device and the adaptor of the invention.

In embodiments, said engagement means includes a proximal inner rim frictionally engageable on the distal tip of a drug delivery device. For example, said distal tip is conical and defines an axial passageway for the transfer of a product contained in said drug delivery device. In embodiments, the inner rim is radially expandable.

In the present application, "user" means a healthcare worker who may need to use the adaptor of the invention in order to connect thereon a needleless access device such as an IV line, or alternatively it may be the drug delivery device manufacturer who will perform the mounting of the adaptor of the invention onto the distal tip of the drug delivery device, so as to provide the drug delivery device with the adaptor already mounted thereon.

Indeed, for example, the adaptor of the invention is usually first mounted onto the distal tip of the drug delivery device by means of its engagement means provided on the proximal region of the globally tubular body engaging the distal tip, for example by friction force. The needleless access device is then threaded into the specific internal thread of the adaptor of the invention. Thanks to this specific internal thread, the connection of the needleless access device onto the adaptor is optimized and the needleless access device may not be disconnected from the adaptor accidently.

In embodiments, the distal tip of the drug delivery device is made of glass. In embodiments, the distal tip is conical and distally tapered.

BRIEF DESCRIPTION OF THE DRAWINGS

The invention and the advantages arising therefrom will clearly emerge from the detailed description that is given below with reference to the appended drawings in which:

FIG. 1 is a cross sectional view of an embodiment of the adaptor of the invention, FIG. 2 is a partial enlarged view of the adaptor of FIG. 1, FIG. 3 is a cross sectional view showing a step of the connection of a needleless access device onto the adaptor of FIG. 1.

DESCRIPTION OF THE INVENTION

Figure 4:
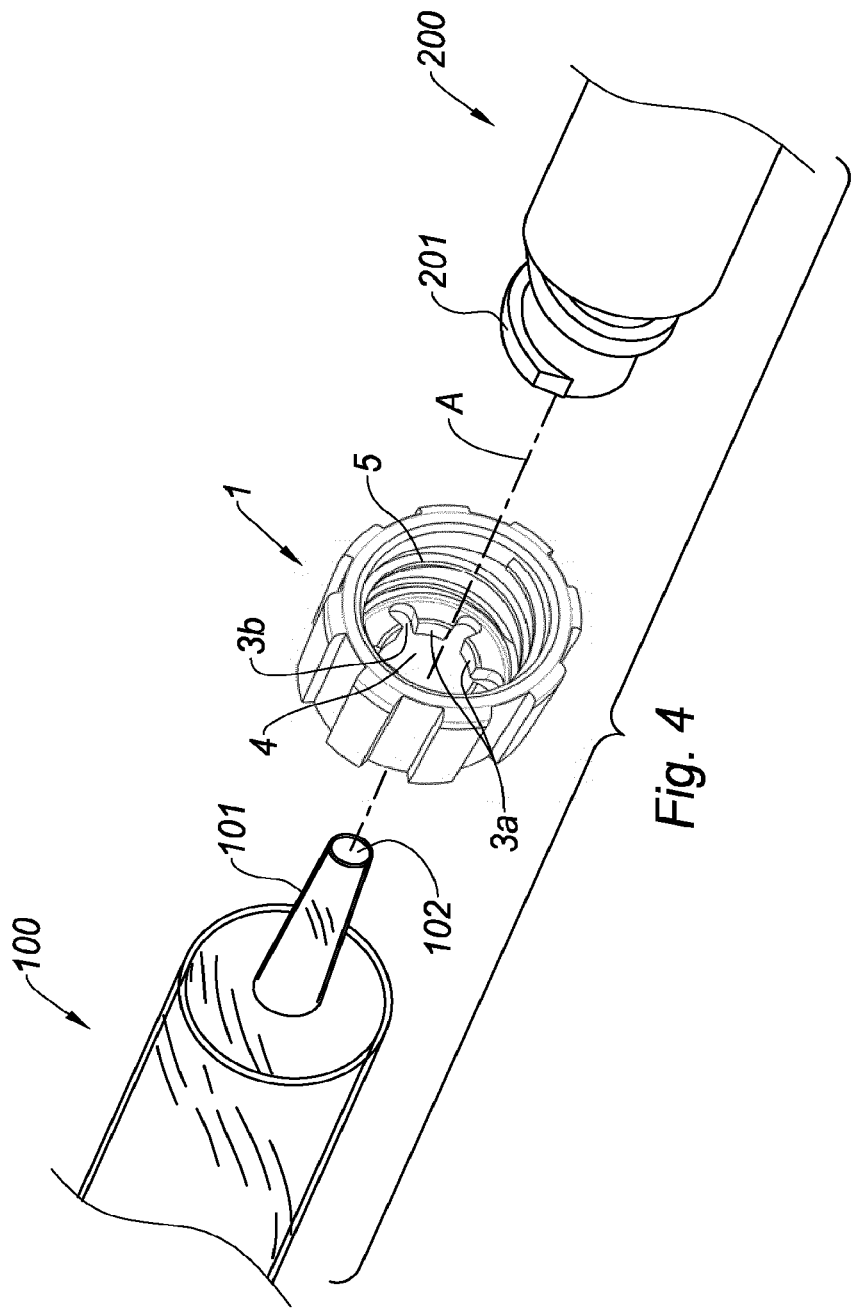
FIG. 4 is an exploded perspective view of the connection of a needleless access device to a drug delivery device via the adaptor of FIG. 1.

With reference to FIG. 1, is shown an adaptor 1 of the disclosure, for connecting a drug delivery device, such as the drug delivery device 100 represented on FIG. 4, to a needleless access device, such as the needleless access device 200 shown on FIGS. 3 and 4.

The adaptor 1 includes a tubular body 2 having a proximal region 2a and a distal region 2b. As will appear from the description below, the adaptor 1 is intended to be connected to the drug delivery device 100 by its proximal region 2a.

In this view, the proximal region 2a of the tubular body 2 is provided with an inner annular rim 3 defining a central bore 4. The inner annular rim 3 is radially expandable so as to fit with friction on the distal tip 101 of the drug delivery device 100. On the example shown, the inner annular rim 3 is formed of a plurality of circumferentially distributed tabs 3a (see also FIG. 4), separated from each other by a plurality of spaces 3b, providing said inner rim 3 with the capability of being expanded radially. As appears from FIG. 4, the distal tip 101 is conical. The annular rim 3 forms engagement means for engaging the adaptor 1 to the distal tip 101 of the drug delivery device 100, as the inner face of the tabs 3a is intended to be in contact with an outer surface of the distal tip 101 when the adaptor 1 is engaged on the distal tip 101, so that the tabs 3a may act as retaining means of the adaptor 1 onto the distal tip 101. In other embodiments not shown, the inner rim could show alternative designs as long as these designs provide flexibility to said rim.

The adaptor 1 may be made of any plastic material providing it with the desired flexibility, such as a material selected from acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations.

The adaptor 1 is intended to be connected to the needleless access device 200 via its distal region 2b.

The distal region 2b of the tubular body 2 is provided on its inner wall with an internal thread 5 extending on a length L measured along longitudinal axis A of said tubular body 2. The internal thread 5 defines peaks 6 and valleys 7 on said inner wall. The major diameter of an internal thread is classically defined as the diameter defined by the valleys.

On the example shown, as better visible on FIGS. 1 and 2, the internal thread 5 includes a proximal part 5a having a length L4, a distal part 5b having a length L1 and a tapered portion 5c linking the proximal part 5a to the distal part 5b, the tapered portion 5c having a length L2. L1, L2 and L4 are measured along longitudinal axis A, and the overall length L of the internal thread 5 corresponds to the addition of L, L2 and L4. None of the lengths L, L1, L2 and L4 is equal to 0. For example, L1 may range from 1.9 mm to 2.1 mm, L2 may range from 1.9 mm to 2.1 mm, L4 may range from 2.35 mm to 2.55 mm.

The distal part 5b of the internal thread 5 defines a major diameter D1 while the proximal part 5a of the internal thread defines a major diameter D2. As appears from FIGS. 1 and 2, D2 is strictly less than D1. As shown on FIGS. 1 and 2, the value of the major diameter of the tapered portion 5c of the internal thread 5 varies from that of D1 to that of D2. D2 has a constant value over the length L4. The proximal part 5a of the internal thread 5 is therefore a straight internal thread on length L4.

With reference to FIG. 3, D1 is the major diameter of the internal thread 5 which is intended to mate the major diameter D3 of the straight external thread 201 provided on the needleless access device 200. Indeed, D1 is identical to D3, so that the straight external thread 201 and the distal part 5b of the internal thread 5 of the adaptor 1 cooperate by regular screwing for threaded engagement. D1 has a constant value over the length L1. The distal part 5b of the internal thread 5 is therefore a straight internal thread on length L1. In the present application, "Straight external thread" means a ridge wrapped around a cylinder in the form of a helix. In particular, the height of the ridge and the diameter of the cylinder are both constant values. In the present application, "straight internal thread" means a ridge located on the inner wall of a tube in the form of a helix. In particular, the height of the ridge and the inner diameter of the tube are both constant values.

In the example shown on FIG. 3, the straight external thread 201 defines peaks 202 and valleys 203. The major diameter D3 of the external thread 201 is the diameter defined by the peaks 202 and it is constant over the whole length L3 of the external thread 201. The length L3 of the external thread 201 corresponds globally to the length L of the internal thread 5 of the adaptor 1.

The needleless access device 200 of FIGS. 3 and 4 is shown partially. The straight external thread 201 forms the proximal end of the needleless access device 200. The needleless access device 200 may be any device intended to be connected to the adaptor 1, either for allowing the transfer of a product from the drug delivery device to another medical device free of needle, such as a pocket drip, a vial, an IV (Intra Venous) line, an IM (Intra Muscular) line, a catheter, or on the contrary for safely closing the filled drug delivery device before its use and for preventing any contamination, like for example a closure cap in the storage position of the drug delivery device.

Since D2 is smaller than D1, the proximal part 5a of the internal thread 5 does not have the correct dimensions for a conventional threaded engagement with the straight external thread 201, the consequences of which will clearly appear later in the description. Preferably, the ratio of D2 to D1 ranges from 0.95 to 0.98.

Preferably, the ratio of the length L1 of the distal part 5b of the internal thread 5 to the length L2 of the tapered portion 5c measured along the direction of the longitudinal axis A of said tubular body 2 ranges from 0.9 to 1.1, preferably is about 1. In embodiments, the ratio of the length L1 of the distal part 5b to the length L4 of the proximal part 5a ranges from 1.125 to 1.325, preferably is about 1.225. In embodiments, the ratio of the length L2 of the tapered portion 5c to the length L4 of the proximal part 5a ranges from 1.125 to 1.325, preferably is about 1.225.

As shown on FIG. 4, the adaptor 1 of FIGS. 1-3 is intended to connect the drug delivery device 100 to the needleless access device 200. The connection of the needleless access device 200 to the drug delivery device 100 will now be described with reference to FIGS. 1-4.

The drug delivery device 100 and the adaptor 1 are aligned and have a common longitudinal axis A. The distal tip 101 of the drug delivery device is conical, distally tapered and it defines an axial passageway 102 for the transfer of a product (not shown) contained therein. The axial passageway 102 is open at its distal end. In embodiments not shown, the outer surface of the distal tip 101 may be provided with an annular groove, or alternatively an annular ridge.

The distal tip 101 may be made of plastic or glass material. In embodiments, the distal tip 101 is made of glass material. In another embodiment, the distal tip 101, as well as the drug delivery device 100, is made of plastic material selected from crystal clear polymer (CCP), acrylonitrile butadiene styrene (ABS), polycarbonate (PC), polystyrene (PS), polypropylene (PP), polyethylene (PE), polyamide (PA) and their combinations.

In a first step, the adaptor 1 is engaged on the distal tip 101 of the drug delivery device 100 by means of its radially expandable inner rim 3. This step is rendered easy to perform due to the distally tapered shape of the distal tip 101 and to the capability of the inner rim 3 to expand radially. In an embodiment not shown, the engagement of the adaptor and its correct positioning is possible thanks to its appropriate fitting with an annular groove located on the distal tip of the drug delivery device. In other embodiments not shown, the adaptor may be maintained in the proximal part of the distal tip of the drug delivery device thanks to an annular ridge.

With reference to FIG. 4, the adaptor 1 is then secured on the distal tip 101 of the drug delivery device 100 by friction fitting of the inner rim 3 on the distal tip 101. In particular, the tabs 3a of the inner rim 3 exert a radial inward force on the outer face of the distal tip 101 and they limit the rotation and the translation of the adaptor 1 with respect to the distal tip 101.

The user then seizes the needleless access device 200 and screws the straight external thread 201 into the internal thread 5 of the adaptor 1. He first screws the straight external thread 201 in the distal part 5b of the internal thread 5 by regular and conventional screwing, as D1 and D3 mate and as the distal part 5b of the internal thread 5 defines a straight internal thread. Then as the tapered portion 5c and the proximal part 5a of the internal thread 5 have different diameters, in particular less than the value of D1, the major diameter of the internal thread 5 on the length L2 of the tapered portion 5c and on the length of the proximal part 5a does not perfectly mate the major diameter D3 of the straight external thread 201 anymore. This difference leads to an increase of the friction between the straight external thread 201 and the tapered portion 5c and proximal part 5a of the internal thread 5 without preventing the complete screwing of the straight external thread 201 in the adaptor 1. Indeed, the screwing remains possible up to the proximal end of the internal thread 5 of the adaptor 1 and the user does not need to increase significantly the torque he exerts in order to obtain a greater friction between the external thread 201 and the internal thread 5. As a consequence, the risks that the adaptor 1 rotates with respect to the distal tip 101 at the time the needleless access device 200 is screwed into the adaptor 1 are greatly limited.

Then, the user continues screwing the needleless access device 200 into the adaptor 1 on the whole length L of the internal thread 5 until the proximal end of the needleless access device 200 reaches the proximal end of the proximal part of the internal thread 5.

Surprisingly, the decrease of the major diameter of the internal thread 5 in its proximal part, and for example in its tapered portion, allows a better friction force of the straight external thread of the needleless access device into the adaptor of the invention, and a more stable resulting connection, without having to exert a higher torque for screwing the needleless access device into the adaptor and without preventing the external thread 201 of the needleless access device to be screwed up to the proximal end of the internal thread 5 of the adaptor 1.

In particular, when the ratio of D2 to D1 ranges from 0.95 to 0.98, the screwing is soft and progressive. Preferably, the ratio of the length L1 of the distal part to the length L2 of the tapered portion ranges from 0.9 to 1.1, preferably is about 1. The resulting connection is particularly stable and secure.

The risks that the needleless access device 200 screwed into the adaptor 1 of the invention be spontaneously disconnected are therefore greatly limited, even when the distal tip is made of glass or when the needleless access device includes spring biased piece providing high counter forces against the connection. The adaptor of the invention therefore allows a reproducible and safe connection of a needleless access device on said adaptor allowing a secured and reliable passage of fluid from the drug delivery device and the needleless access device. Further, the adaptor of the invention may be compatible with lots of available connectors of the market.

In addition, the decrease of the major diameter of the internal thread 5 in the proximal part of said internal thread 5 provides for a thicker wall of the proximal part of the tubular body 2, thereby increasing the resistance of said body 2 at the time the needleless access device 200 is screwed therein. Therefore, the adaptor is more resistant.

The adaptor of the invention allows the reliable connection of a needleless access device on the distal tip of a drug delivery device. The risks that the needleless access device unscrews spontaneously and accidently from the adaptor of the invention are very limited.

What is claimed is:

1. A needleless access device assembly, comprising:
   a needleless access device provided with a straight external thread, said straight external thread having a major diameter of constant value over the whole length of said straight external thread; and
   an adaptor for connecting a drug delivery device to the needleless access device, the adaptor comprising:
      a globally tubular body having a proximal region and a distal region, said proximal region being provided with an engagement element for mounting said adaptor on the drug delivery device, said distal region being provided on its inner wall with an internal thread cooperating with said external thread on a determined length of said internal thread, said internal thread having on a distal part of said length, said distal part having a first length, a first major diameter of constant value mating that of said straight external thread, wherein said internal thread has, on a proximal part of said first length, a second major diameter, where the second major diameter is strictly smaller than the first major diameter, the proximal part of the internal thread being configured for cooperating with the same straight external thread as the distal part of the internal thread, wherein said internal thread further comprises a tapered portion linking said proximal part to said distal part, said tapered portion having a second length and said tapered portion of the internal thread being configured for cooperating with the same external thread as the distal part and the proximal part of the internal thread.

2. The needleless access device assembly according to claim 1, wherein the ratio of the second major diameter to the first major diameter ranges from 0.95 to 0.98.

3. The needleless access device assembly according to claim 1, wherein said proximal part having a third length, the second major diameter having a constant value over the third length.

4. The needleless access device assembly according to claim 1, wherein the ratio of the first length of the distal part to the second length of the tapered portion ranges from 0.9 to 1.1.

5. The needleless access device assembly according to claim 1, wherein said engagement element comprises a proximal inner rim frictionally engageable on the distal tip of the drug delivery device.

6. The needleless access device assembly according to claim 5, wherein the inner rim is radially expandable.

7. The needleless access device assembly according to claim 1, wherein the ratio of the first length of the distal part to the third length of the proximal part ranges from 1.125 to 1.325.

8. The needleless access device assembly according to claim 1, wherein the ratio of the second length of the tapered portion to the third length of the proximal part ranges from 1.125 to 1.325.

9. The needleless access device assembly according to claim 1, wherein the needleless access device further comprises the drug delivery device comprising a distal tip defining an axial passageway for the transfer of a product contained in said drug delivery device, the adaptor being mounted on said distal tip.

10. The needleless access device assembly according to claim 9, wherein the distal tip is made of glass.

11. The needleless access device assembly according to claim 9, wherein the distal tip is conical and distally tapered.

12. An adaptor for connecting a drug delivery device to a needleless access device provided with a straight external thread, the adaptor comprising:
   a globally tubular body having a proximal region and a distal region, said proximal region being provided with an engagement element for mounting said adaptor on the drug delivery device, said distal region being provided on its inner wall with an internal thread intended to cooperate with said external thread on a determined length of said internal thread so as to connect said needleless access device to said adaptor, said internal thread having on a distal part of said determined length, said distal part having a first length, a first major diameter of constant value mating that of said straight external thread, wherein said internal thread has on a proximal part of said determined length a second major diameter, where the second major diameter is smaller than the first major diameter, wherein said internal thread further comprises a tapered threaded portion linking said proximal part to said distal part, said tapered threaded portion having a second length, the internal thread being configured to increase the friction between the straight external thread and the tapered threaded portion and the proximal part of this internal thread, the proximal part, the tapered threaded portion and the distal part of the internal thread being configured to cooperate simultaneously with the same straight external thread of the needleless access device, wherein the ratio of the first length of the distal part to the second length of the tapered portion ranges from 0.9 to 1.1.

13. The adaptor according to claim 12, wherein the ratio of the second major diameter to the first major diameter ranges from 0.95 to 0.98.

14. The adaptor according to claim 12, wherein said proximal part having a third length, the second major diameter has a constant value over the third length.

15. The adaptor according to claim 12, wherein said engagement element comprises a proximal inner rim frictionally engageable on the distal tip of the drug delivery device.

16. The adaptor according to claim 15, wherein the inner rim is radially expandable.

17. The adaptor according to claim 14, wherein the ratio of the first length of the distal part to the third length of the proximal part ranges from 1.125 to 1.325.

18. The adaptor according to claim 14, wherein the ratio of the second length of the tapered portion to the third length of the proximal part ranges from 1.125 to 1.325.

19. A drug delivery device comprising:
   a distal tip defining an axial passageway for the transfer of a product contained in said drug delivery device, and
   at least one adaptor according to claim 12 mounted on said distal tip.

20. The drug delivery device according to claim 19, wherein the distal tip is made of glass.

21. The drug delivery device according to claim 19, wherein the distal tip is conical and distally tapered.

22. The needleless access device assembly according to claim 1, wherein the straight external thread of the needleless access device defines a third major diameter equal to the first major diameter.

23. The adaptor according to claim 12, wherein the straight external thread of the needleless access device defines a third major diameter equal to the first major diameter.

* * * * *